United States Patent
Yellepeddi et al.

[11] Patent Number: 5,406,608
[45] Date of Patent: Apr. 11, 1995

[54] X-RAY ANALYSIS APPARATUS

[75] Inventors: Ravisekhar Yellepeddi, Ecublens; Alexandre Bapst, Villa St. Pierre; Pierre-Yves Negro, Ecublens, all of Switzerland

[73] Assignee: Fisons plc, Ipswich, United Kingdom

[21] Appl. No.: 150,440

[22] Filed: Nov. 10, 1993

[30] Foreign Application Priority Data

Nov. 11, 1992 [GB] United Kingdom ............... 9223592

[51] Int. Cl.⁶ .................................. G01N 23/223
[52] U.S. Cl. ............................ 378/46; 378/45
[58] Field of Search ............................. 378/46, 45

[56] References Cited

U.S. PATENT DOCUMENTS

| | | | |
|---|---|---|---|
| 3,344,274 | 9/1967 | Ashby et al. | 378/46 |
| 3,903,414 | 9/1975 | Herbstein et al. | 378/46 |
| 4,263,510 | 4/1981 | Ciccarelli et al. | 378/46 |
| 5,107,527 | 4/1992 | Sipila et al. | 378/46 |

Primary Examiner—Craig E. Church
Attorney, Agent, or Firm—Chilton, Alix & Van Kirk

[57] ABSTRACT

A device for performing both elemental and structural analysis of a crystalline sample, comprising a polychromatic x-ray source (11); a mounting means (15) for mounting the sample so that it is illuminated with x-rays; one or more fluorescence channels (17), able to select x-rays of a particular wavelength and energy and having means (20) for detecting said selected x-ray; a diffraction channel (28) able to select a characteristic x-ray wavelength at said source (11) following diffraction of the x-rays by said sample (14) and having means (33) for detecting a selected characteristic x-ray; and an actuating means (32) for controlling arcuate movement of said diffraction channel (28) relative to said sample (14) so as to detect x-rays leaving the sample at different diffraction angles.

15 Claims, 4 Drawing Sheets

X-RAY ANALYSIS APPARATUS

The present invention relates to the analysis of materials by the use of X-rays, and in particular to a device able to obtain both elemental and crystallographic analysis in a single instrument.

Diffractometers and spectrometers are known in the prior art and may be used to determine the structural and elemental characteristics respectively of a material having a crystalline nature. These instruments provide for the identification of unknown samples in many industrial applications.

Diffraction occurs when the wavelength of the incident radiation is comparable to or less than the separation of the crystal planes. Such a photon beam is required to have a photon energy in the x-ray region to achieve significant diffraction by the crystal planes. The path difference for diffracted rays is described by the Bragg Law:

$$n\lambda = 2d_{hkl} \sin \theta_1 \qquad (1)$$

where n is an integral number of wavelengths $\lambda$, $\theta_1$ is the angle of diffraction and $d_{hkl}$ is the interplanar distance dependent on the Miller indices h, k and l of the crystal.

The Bragg law requires that $\theta$ and $\lambda$ be matched; in order to satisfy this relation it is necessary to have a range of wavelengths or angle. For a single crystal this may be achieved by the use of a polychromatic x-ray beam or by rotating the crystal in a monochromatic beam. In the majority of cases, however, the sample is polycrystalline leading to a continuum of crystallite orientations. In this case it is necessary to use an incident beam of monochromatic x-rays to obtain a well resolved diffraction pattern.

Prior art x-ray diffractometers incorporate the following features:

1) a collimated monochromatic radiation source (typically a copper source which has an intense characteristic x-ray line at 1.5418 Å (8.043 keV)); 2) a sample manipulator and support; 3) a detection system to measure the diffracted radiation.

The diffraction information allows identification of the crystallographic planes of the sample material but does not enable determination of the chemical composition.

In order to obtain an elemental analysis of a material it is necessary to employ a different technique. The sample may be investigated either chemically or by a spectroscopic method. Chemical methods such as titration are often unsuitable due to the inaccuracy and destructive nature of such tests. Accurate elemental information may be obtained by use of the phenomenon of x-ray fluorescence (XRF). Bombardment of a sample by an x-ray beam causes the emission of secondary x-rays with wavelengths characteristic of the constituent elements of the material. The production of secondary x-rays is determined by the electronic structure of the material which varies from element to element. In order to construct an x-ray spectrometer that is useful over a range of elements it is necessary to use a polychromatic x-ray source producing a wide range of x-ray wavelengths.

The principal features of a prior art wavelength dispersive x-ray fluorescence spectrometer are:

1) a divergent polychromatic x-ray source; 2) a dispersive device based on flat crystal diffraction (parallel beam optics) or curved crystal diffraction (focused beam optics) to separate the fluorescence spectrum from the sample into discrete monochromatic wavelengths; 3) a detection system (such as a gas filled counter or scintillation detector) to measure the intensity of the individual spectral lines.

The information obtained from this device provides a quantitative analysis of the elements present in the sample. The x-ray fluorescence spectrometer is not able to provide information regarding the chemical or crystallographic phases of the sample since the fluorescence process is insensitive to these factors.

It may be seen that the requirements for XRF analysis are very different from those for XRD studies. Since it is desirable to provide both techniques in a single instrument, such devices are known in the prior art. A device is disclosed in U.S. Pat. No. 3,344,274 which incorporates two x-ray sources into a common housing, wherein one source is suitable for XRD and the other source for XRF. Another device, which may be used to provide both structural and elemental information, is described in European Patent No 183,043. This apparatus uses a single x-ray source which may be directed directly onto the sample for XRF analysis or may be monochromated prior to interaction with the sample in order to provide a source suitable for XRD analysis.

The use of two x-ray sources is undesirable due to the expense of providing two such sources. The device of European Patent No 183,043 makes use of a complex arrangement of goniometers in order to produce an apparatus capable of both XRF and XRD analysis. This can result in difficulties due to the precision and reproducibility necessary when the geometry of the device is changed.

It is an object of the present invention to provide an x-ray analysis instrument capable of both x-ray diffraction and x-ray fluorescence and requiring only the use of a single source.

It is a further object of the invention to provide an x-ray analysis instrument requiring only a single sample support and sample introduction mechanism.

It is a yet further object of the invention to provide an x-ray analysis instrument which does not require a high degree of complexity or precision to change between the two techniques of x-ray analysis.

According to the invention there is provided a device for performing both elemental and structural analysis of a crystalline sample, said device comprising:

a) a polychromatic x-ray source;
b) a mounting means for mounting the sample so that it is illuminated with x-rays;
c) one or more fluorescence channels able to select x-rays of a particular wavelength and energy and having means for detecting said selected x-rays;
d) a diffraction channel able to select a characteristic x-ray wavelength of said source following diffraction of the x-rays by said sample and having means for detecting said selected characteristic x-rays; and
e) an actuating means for controlling arcuate movement of said diffraction channel relative to said sample so as to detect x-rays leaving the sample at different diffraction angles.

The device of the present invention provides an apparatus wherein both x-ray fluorescence and x-ray diffraction may be performed on the same sample using a single x-ray source. It is not necessary to change the geometry of the device when changing between elemental and structural analysis.

A number of embodiments of the invention will now be described by way of example only and with reference to the accompanying drawings in which.

Figure 1:
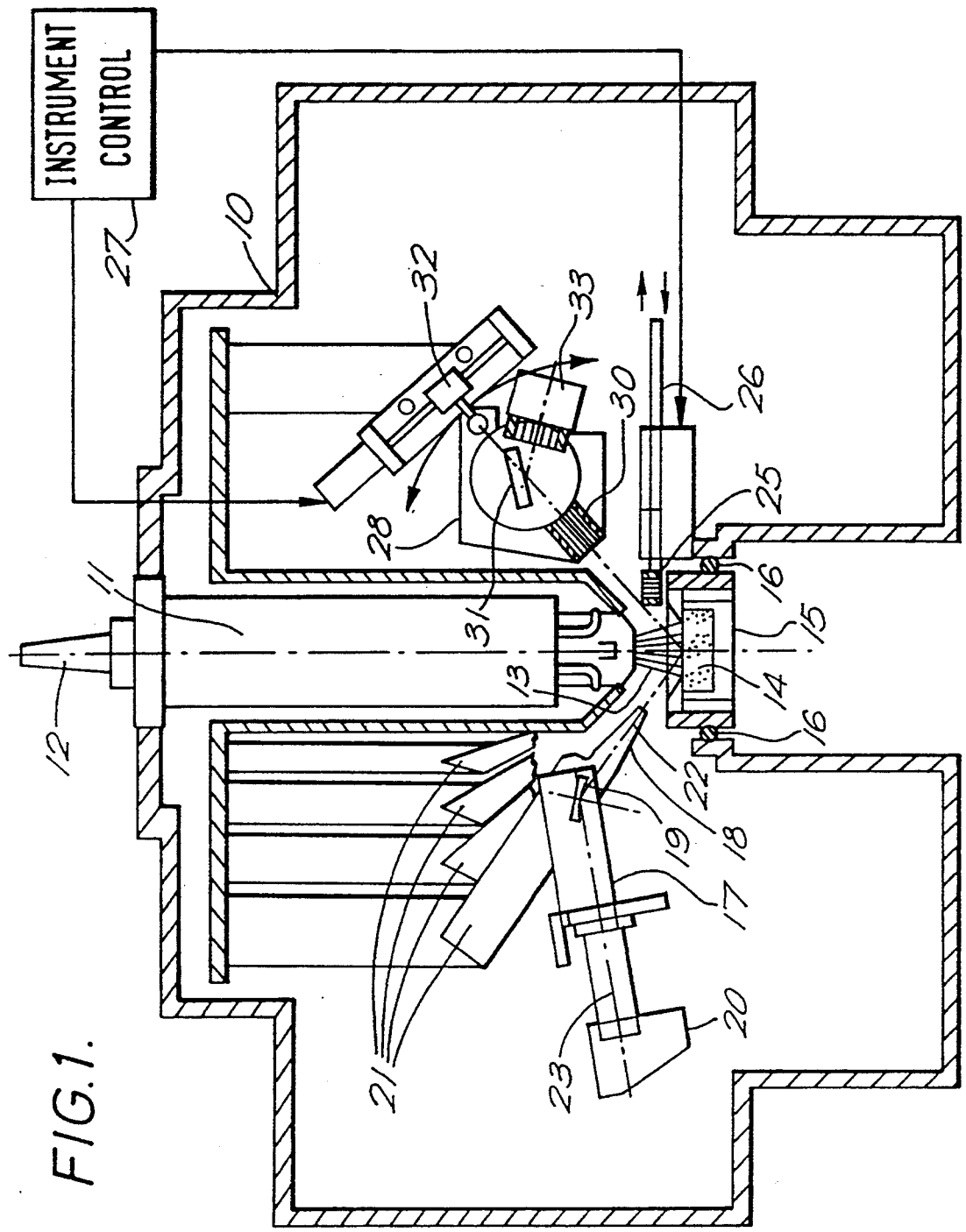
FIG. 1 shows a section of an embodiment of the invention.

FIG. 1 illustrates an embodiment of the present invention in a mode particularly suitable for x-ray fluorescence analysis. In this schematic drawing, a vacuum chamber 10 contains the x-ray apparatus. The polychromatic x-ray source 11 is mounted on the vacuum chamber 10 and electrical voltages supplied through feedthrough 12. The x-rays are emitted from source 11 in a divergent beam 13. The energy distribution of the x-rays emitted from source 11 is determined by the target material of the x-ray anode. Commonly used target materials known in the art include copper, tungsten, rhodium, molybdenum and gold. The choice of x-ray target is determined by requirements of the materials to be studied. The divergent x-ray beam 13 strikes the polycrystalline sample 14 causing the emission of secondary x-rays and diffraction of the incident beam. The sample 14 is held in place by sample holder 15 which may be removed to allow the sample to be changed. The integrity of the vacuum is maintained by seal 16 between the chamber 10 and the sample holder 15. The secondary and diffracted x-rays are restricted by the x-ray source 11 and vacuum chamber 10 so that they are emitted in the form of a hollow cone. Such an arrangement allows the placement of instrumentation, including fluorescence channel 17 and diffraction channel 28, in the complete 360° around the x-ray source 11.

The energy of fluorescence x-rays emitted from the sample 14 are characteristic of the elemental composition of the material. Such x-rays must be separated from the continuum of x-ray energies by some means before detection takes place. It is well known in the art that energy selection may be obtained by means of Bragg reflection from the surface of a crystal. A schematic representation of a static fluorescence channel 17 which uses this principle may be seen in FIG. 1. The channel 17 consists of an entry housing 18, a curved crystal 19 and an x-ray detector 20, the channel 17 being held in place by a support 21. The figure also shows further supports 21 which may be used to hold other fluorescence channels. X-rays 22 from the sample pass into the entry 18 and impinge on the curved crystal 19 which acts to monochromate and focus a beam 23 of x-rays of the desired energy onto detector 20. The detector 20 will typically be a gas-filled counter or scintillation detector. A number of static fluorescence channels 17 may be employed in order to simultaneously select and measure fluorescence x-rays of differing energies. The use of static fluorescence channels is well suited to applications where the same elemental constituents are always present but where a requirement exists for monitoring the proportions present. An example of this is in the industrial production of steel or cement where the elemental proportions are dictated by international standards.

The advantage of a plurality of static fluorescence channels lies in their ability to focus and measure several characteristic x-ray energies simultaneously. This system is however inflexible and may only measure the presence of certain chosen elements. To overcome this difficulty it is common to use a sequential fluorescence channel such as a goniometer-mounted fluorescence channel. This device comprises a flat diffraction crystal mounted on a goniometer. The goniometer allows sequential scanning of x-ray energy to determine sample composition. The embodiment of the invention shown in FIG. 2 incorporates such a goniometer-mounted fluorescence channel 24 containing a collimator 34, flat crystal 35, goniometer 36 and detector 37 and held in place by a support 21 from the vacuum chamber 10. Since both intensity and speed are reduced in such a device it may be desirable to include both static and goniometer-mounted fluorescence channels 17, 24 in the same instrument.

The positions of the flat crystal 35 and detector 37 may advantageously be independently controlled by means of an optically coupled goniometer operating on the principle of Moire fringe interference. The positions of both crystal 35 and detector 37 are measured by means of electro-optical readers which count Moire fringes resulting from interference between a grating in the reader and a fixed radial grating. Such an optically coupled goniometer does not require gearing and increases reproducibility.

The divergent x-ray beam 13 may, if required, be collimated by a primary collimator 25 which is mounted on actuating means 26. Control means 27 are used to control the movement of the actuating means 26 into and out of the x-ray beam. The primary collimator 25 may advantageously be constructed so that the collimation obtained is variable both in its orientation with respect to the sample surface and in its divergence. Variation of the orientation of the primary collimator 25 allows different crystallographic planes to diffract within the given angular range, whereas variation of the divergence admitted by primary collimator 25 allows the resolution of the diffraction spectrum to be altered. Such a change of collimation might be achieved by the use of a selection of collimators any of which may be placed in the primary beam or by mechanical adjustment of the orientation of the collimator, or the distance between collimator plates in a single such collimator. A means for adjusting the orientation and/or the degree of collimation would preferably be incorporated into the actuating means 26. FIG. 3 shows an expanded view of the diffraction channel 28 illustrated in FIGS. 1 and 2. The primary collimator 25 is shown in the x-ray beam in FIG. 3 and produces a parallel beam 29 of x-rays which illuminate the sample.

The characteristic x-rays may be several orders of magnitude more intense than the continuum so that the diffracted beam will be dominated by the characteristic wavelengths. Since the sample will in general contain several crystallographic phases with different interplanar spacings, the resulting diffraction pattern is complex with further complexity added by the presence of fluorescence x-rays. The diffraction channel 28 aims to discriminate the different wavelengths present in the beam so as to produce a diffraction pattern capable of analysis.

Referring to FIG. 3, the diffracted x-ray beam is collimated by a secondary collimator 30 and directed onto a monochromating diffraction crystal 31. The secondary collimator 30 is placed at a specific angle relative to the sample shown by the angle $(2\theta_1-90°)$ in FIG. 3, where $\theta_1$ is the angle of diffraction defined in equation 1. The angle $2\theta_1$ is referred to as the take-off angle and may be changed by angular actuating means 32. The angular actuating means 32 changes the angle of diffraction channel 28, which consists of secondary collimator 30, monochromator crystal 31 and detector 33, and is controlled by instrument control means 27 outside the vacuum chamber 10. The monochromator crystal 31 is positioned at an angle $\theta_2$ relative to the diffracted beam such that a chosen characteristic wavelength from the x-ray source 11 is selected and passes into detector 33. In this way almost all fluorescence x-rays and unwanted diffraction peaks are eliminated and a diffraction pattern of the sample may be obtained by scanning of the angular actuating means 32. The detected photons are counted and processed by electronic means (not shown) to provide a diffractogram. Any accidental degeneracies which enter the detector 33 will ordinarily be insignificant due to the high intensity of the selected wavelength.

Figure 2:
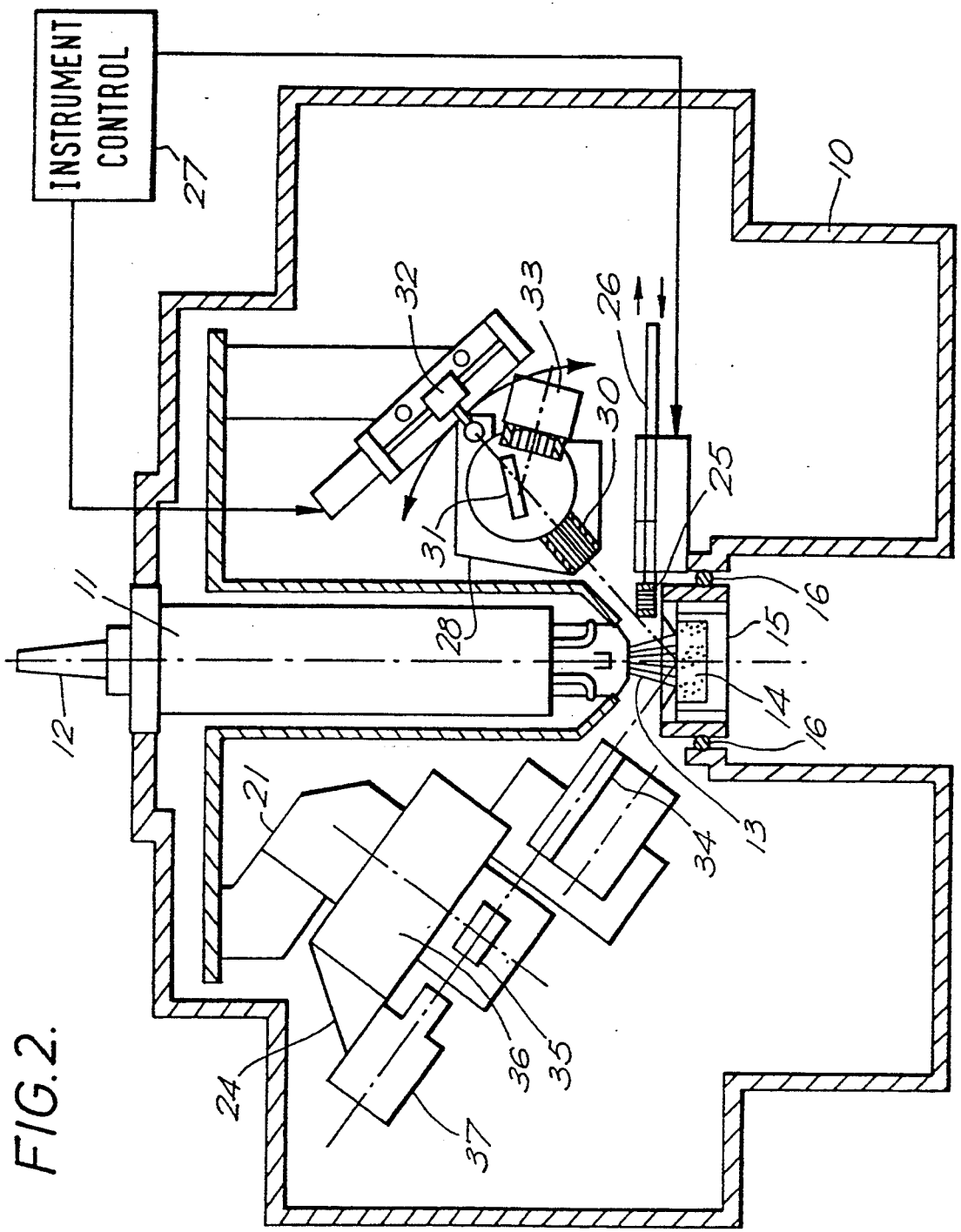
FIG. 2 shows a section of a further embodiment according to the invention.
Figure 3:
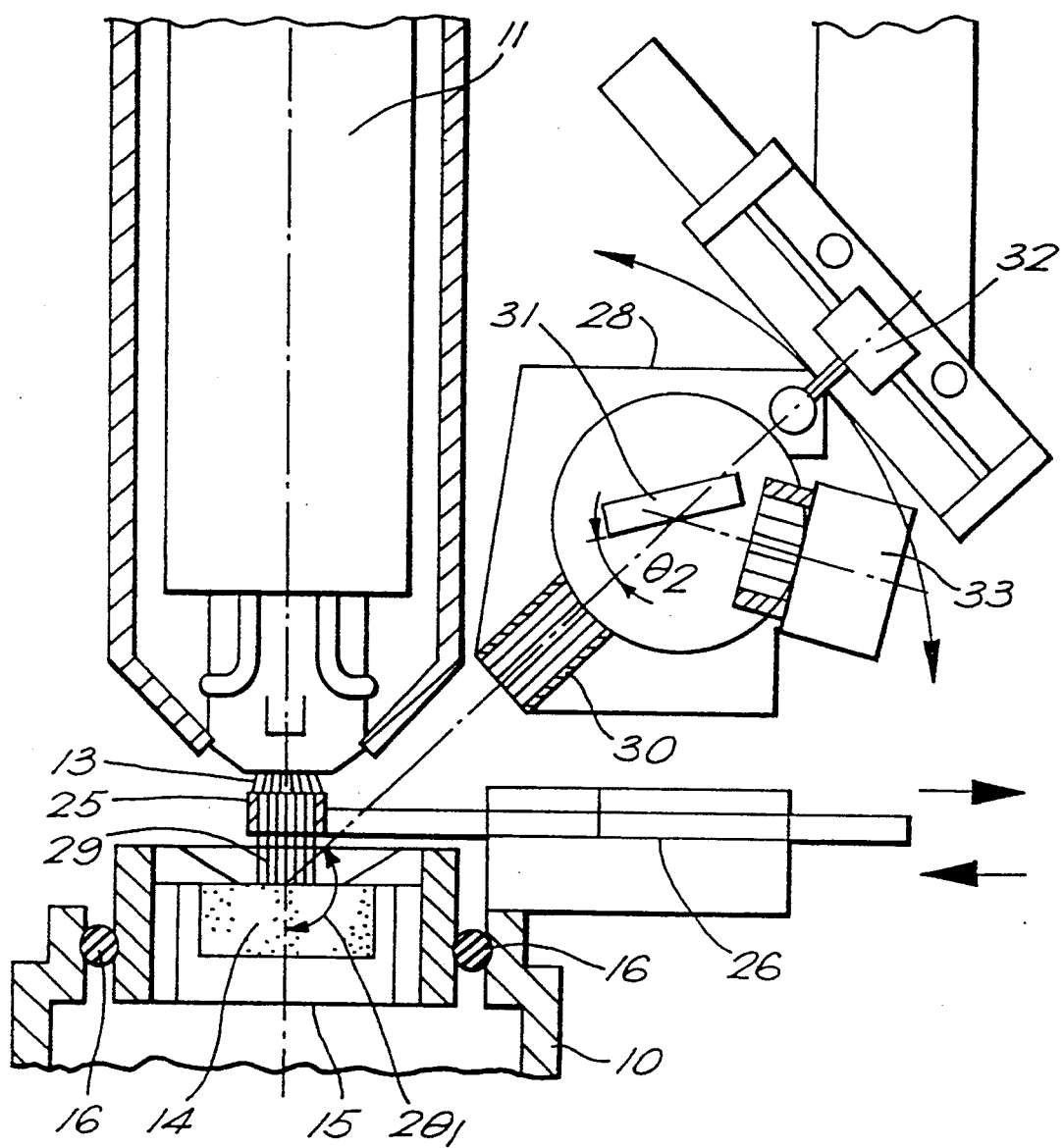
FIG. 3 shows a section of an embodiment of a diffraction channel according to the invention.

The geometry adopted in FIGS. 1 and 2 allows the placement of an x-ray diffraction channel 28 in addition to a plurality of static and goniometer-mounted fluorescence channels 17, 24. The choice of how many channels and over what energy range they operate will be determined by the particular application.

Figure 4A:
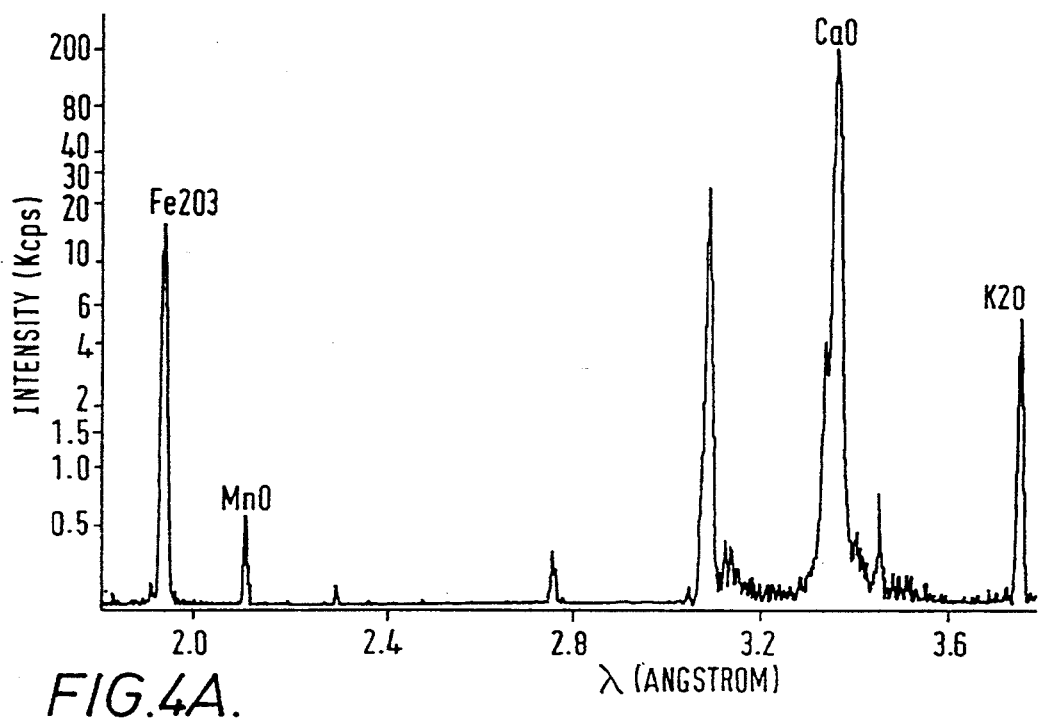
FIG. 4A shows an example of an x-ray fluorescence spectrum obtained from an embodiment of the invention.
Figure 4B:
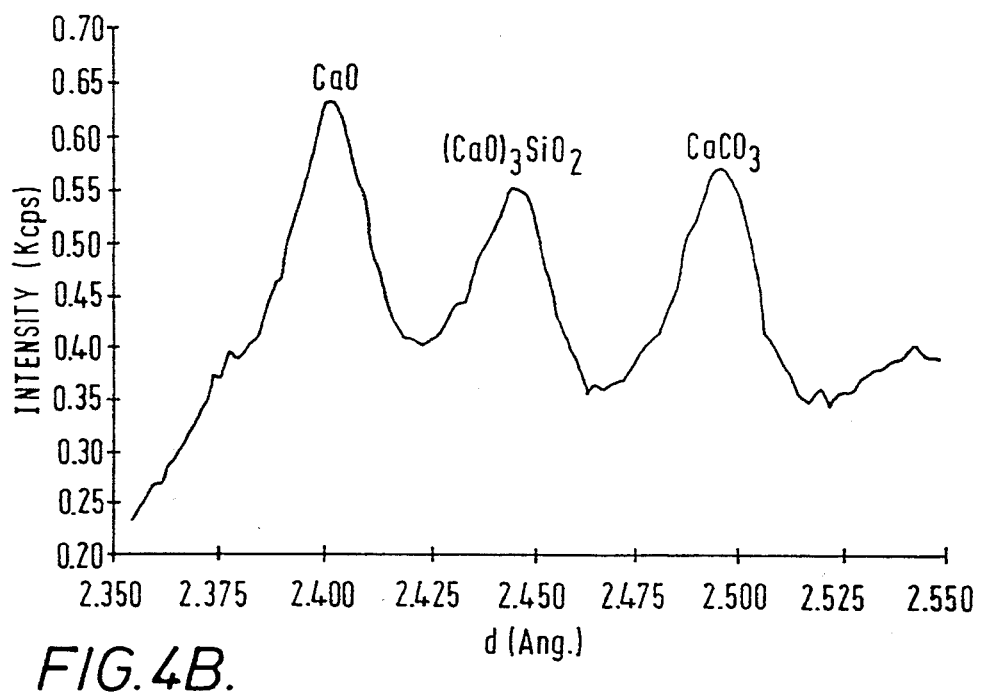
FIG. 4B shows an example of an x-ray diffraction spectrum obtained from an embodiment of the invention.

FIGS. 4A and 4B illustrate an example of the usefulness of the invention in relation to cement clinkers.

The x-ray fluorescence spectrum shown in FIG. 4A is typical of the results obtained from a cement clinker. The peak marked CaO represents the total CaO concentration present independent of mineralogical form. Quality requirements make necessary a knowledge not only of the CaO content but also of its structural nature. The use of the diffraction channel of the invention, shown by the diffractogram in FIG. 4B, enables monitoring of the free lime (CaO), limestone ($CaCO_3$) and other phases of CaO within the clinker sample so that such requirements may be met.

As can be seen, the present invention provides an x-ray analyser which allows both fluorescence and diffraction measurements to be made in the same instrument. The invention provides a significant advance over the prior art since only a single x-ray source is required and in addition no large scale realignments of the components of the device are necessary when changing between the two modes of operation.

We claim:

1. A device for performing both elemental and structural analysis of a crystalline sample, said device comprising:
   a) a polychromatic x-ray source;
   b) a mounting means for mounting the sample so that it is illuminated with x-rays;
   c) one or more fluorescence channels able to select x-rays of a particular wavelength and energy and having means for detecting said selected x-rays;
   d) a diffraction channel able to select a characteristic x-ray wavelength of said source following diffraction of the x-rays by said sample and having means for detecting said selected characteristic x-rays; and
   e) an actuating means for controlling arcuate movement of said diffraction channel relative to said sample so as to detect x-rays leaving the sample at different diffraction angles.

2. A device as claimed in claim 1 wherein one or more of the fluorescence channels is a static channel having a curved focusing crystal as the x-ray selecting means.

3. A device as claimed in claim 1 wherein one or more of the fluorescence channels is a sequential channel having a goniometer-mounted flat crystal as the x-ray selecting means.

4. A device as claimed in claim 3 wherein the flat crystal and detecting means may be independently positioned by means of an optically coupled goniometer.

5. A device as claimed in claim 3 comprising a combination of one or more static channels and one or more sequential channels.

6. A device as claimed in claim 1 wherein the diffraction channel has means for selecting diffracted characteristic x-rays, comprising a collimator and a diffraction crystal.

7. A device as claimed in claim 1 having a means for collimating the x-ray beam between the source and the sample.

8. A device as claimed in claim 7 having means for changing the degree of collimation of the x-ray beam.

9. A device as claimed in claim 7 having means for changing the orientation of the collimation of the x-ray beam.

10. A device as claimed in claim 7 wherein the said collimating means may be moved into and out of the x-ray beam by an actuating means.

11. A device as claimed in claim 1 wherein the fluorescence and diffraction channels are disposed to receive radiation emitted generally into a conical shell having its axis generally along the direction of the x-ray beam between the source and the sample.

12. A device as claimed in claim 2 wherein one or more of the fluorescence channels is a sequential channel having a goniometer-mounted flat crystal as the x-ray selecting means.

13. A device as claimed in claim 12 wherein the flat crystal and detecting means may be independently positioned by means of an optically coupled goniometer.

14. A device as claimed in claim 8 wherein the said collimating means may be moved into and out of the x-ray beam by an actuating means.

15. A device as claimed in claim 9 wherein the said collimating means may be moved into and out of the x-ray beam by an actuating means.

* * * * *